(12) United States Patent
Chon et al.

(10) Patent No.: US 10,285,601 B2
(45) Date of Patent: *May 14, 2019

(54) DETECTION AND MONITORING OF ATRIAL FIBRILLATION

(71) Applicant: Worcester Polytechnic Institute, Worcester, MA (US)

(72) Inventors: Ki H. Chon, Worcester, MA (US); Jowoon Chong, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,912

(22) Filed: May 22, 2018

(65) Prior Publication Data

US 2018/0271389 A1     Sep. 27, 2018

Related U.S. Application Data

(63) Continuation of application No. 14/702,601, filed on May 1, 2015, now Pat. No. 9,986,921.

(60) Provisional application No. 61/987,057, filed on May 1, 2014.

(51) Int. Cl.
| | |
|---|---|
| *A61N 5/02* | (2006.01) |
| *A61B 5/024* | (2006.01) |
| *A61B 5/00* | (2006.01) |
| *A61B 5/0464* | (2006.01) |

(52) U.S. Cl.
CPC ........ *A61B 5/02405* (2013.01); *A61B 5/0464* (2013.01); *A61B 5/6898* (2013.01); *A61B 5/7282* (2013.01)

(58) Field of Classification Search
CPC . A61B 5/02405; A61B 5/0464; A61B 5/6898; A61B 5/7282
See application file for complete search history.

(56) References Cited

U.S. PATENT DOCUMENTS

| | | |
|---|---|---|
| 8,560,058 B2 | 10/2013 | Babaeizadeh et al. |
| 2008/0161706 A1 | 7/2008 | Cho et al. |
| 2011/0166466 A1 | 7/2011 | Chon et al. |
| 2012/0283579 A1 | 11/2012 | Briggs et al. |
| 2013/0102864 A1 | 4/2013 | Sacco et al. |
| 2013/0144180 A1 | 6/2013 | Chon et al. |
| 2013/0218037 A1 | 8/2013 | Raeder |

*Primary Examiner* — Amanda K Hulbert
(74) *Attorney, Agent, or Firm* — Burns & Levinson LLP; Orlando Lopez

(57) ABSTRACT

A real-time arrhythmia discrimination method is used in smartphones, which can discriminate between NSR, AF, PACs and PVCs using pulsatile time series collected from a smartphone's camera. To increase the sensitivity of AF detection and add the new capabilities of PVC and PAC identification, the arrhythmia discrimination method of these teachings combines Root Mean Square of Successive RR Differences (RMSSD), Shannon Entropy (ShE) and turning point ratio (TPR), with the Poincare plot, and utilizes the features of pulse rise/fall time and amplitude for arrhythmia discrimination.

5 Claims, 13 Drawing Sheets

DETECTION AND MONITORING OF ATRIAL FIBRILLATION

CROSS REFERENCE TO RELATED APPLICATIONS

This application Is a continuation of co-pending U.S. patent application Ser. No. 14/702,601, filed on May 1, 2015, entitled DETECTION AND MONITORING OF ATRIAL FIBRILLATION, which claims priority of U.S. Provisional Application Ser. No. 61/987,057, entitled DETECTION AND MONITORING OF ATRIAL FIBRILLATION, filed on May 1, 2014, both of which are incorporated by reference herein in their entirety and for all purposes.

STATEMENT REGARDING FEDERALLY SPONSORED RESEARCH OR DEVELOPMENT

This invention was made with U.S. Government support under grant W81XWH-12-1-0541 awarded by the U.S. Army Medical Research and Material Command. The U.S. Government has certain rights in the invention.

BACKGROUND

These teachings relate generally to methods and systems for detection and monitoring of Atrial Fibrillation (AF).

The prevalence of AF is increasing (20.7 per 1,000 patient years), especially among the growing number of older Americans. At age 55 the lifetime risk for developing AF is approximately 1 in 5 and it is estimated that 16 million individuals may be affected by 2040. The growing population burden of AF has widespread clinical and public health relevance, since AF is closely linked to increased risk for stroke and heart failure, as well as diminished quality of life and longevity. Novel treatments for AF, such as catheter-based ablation, exist but require post-treatment monitoring to establish treatment response. To date, traditional methods of AF detection have been confounded by the often paroxysmal and minimally symptomatic nature of this arrhythmia. Brief, asymptomatic episodes of AF remain associated with increased morbidity and mortality, highlighting the need for sensitive AF screening instruments that do not rely on patient symptoms. Contemporary screening for AF involves the use of continuous ambulatory electrocardiographic monitoring (Holter) or longer-duration symptom-triggered (Event) monitors. The detection of arrhythmias via a smartphone application, on the other hand, could lead to many people self-screening even if asymptomatic, if there was sufficient publicity about the dangers of AF and the application was widely adopted. Certainly the barriers to adoption are very low, as most people perceive using the application as fun, which no one has ever claimed about wearing a Holter monitor. Although monitors with automated AF detection capabilities are increasingly utilized to screen for serious atrial arrhythmias, especially after AF ablation, they are severely limited by motion and noise artifacts and an inability to discriminate between AF and other atrial arrhythmias. The ideal AF detection tool would provide real-time, automatic detection of AF in a sensitive and specific manner. Furthermore, since AF is often associated with the clinically relevant, but distinct, premature beats (PVC and PAC), the ideal AF screening instrument would also be able to recognize PVC and PAC.

Atrial Fibrillation (AF) is the most common sustained dysrhythmia worldwide. Over 2.3 million Americans are currently diagnosed, and the prevalence of AF is increasing with the aging of the U.S. population. Through its association with increased risk for heart failure, stroke, hospitalization and mortality, AF has a profound impact on the longevity and quality of life of a growing number of Americans. Although new AF treatment strategies have emerged over the last decade, a major challenge facing clinicians and researchers is the paroxysmal, often short-lived, and sometimes asymptomatic nature of AF.

Although the population with undiagnosed AF is substantial, studies have shown that more frequent monitoring can improve AF detection. There is therefore a pressing need to develop methods for accurate AF detection and monitoring in order to improve patient care and reduce healthcare costs associated with treating complications from AF. Such a method would have important clinical and research applications for AF screening as well as for assessing treatment response (e.g. after cardioversion or AF ablation). For these reasons, the importance of developing new AF detection technologies was emphasized by a recent NHLBI Expert panel.

Since the standard-of-care for detection of AF relies on the arrhythmia being present during an electrocardiogram (ECG), a great deal of serendipity is required in the diagnosis of this often intermittent arrhythmia. A more effective AF detection strategy requires a readily available and cost-effective monitoring device that could be operated by a patient on a daily basis, combined with an accurate, real-time AF detection algorithm. The ideal AF monitoring device would be accessible, inexpensive, and simple to operate in order to be widely accepted by individuals with, or at risk for, AF.

A smartphone application to measure heart interval series and then use this data to detect AF real-time was previously developed. That approach uses standard phone components and does not require extra hardware, as the optical video monitoring of the skin with the standard digital camera embedded in smartphones is sufficient to detect variability in the heart rate signal (see FIG. 8), indicating that accurate pulse interval data can be obtained. A set of statistical algorithms has been developed that can accurately identify AF using signatures of near-random characteristics in the pulse intervals. That AF detection method is real-time realizable and has demonstrated a sensitivity of 94.4% and specificity of 95.1% for detection of AF beats using data from the MIT-BIH AF database. For clinical applications, however, it is enough to detect AF episodes, and an episode detection rate of 100% has been achieved. In a recent prospective clinical investigation involving 76 participants with AF, it was demonstrated that the smartphone-based AF detection approach discriminated AF from normal sinus rhythm. Although that algorithm is robust for AF detection, a major limitation is that it is not designed to discriminate premature ventricular contractions (PVC) and premature atrial contractions (PAC) from AF. Consequently, that AF algorithm has resulted in false detection of AF in the presence of many PAC/PVC episodes interspersed with normal sinus rhythm (NSR) because the presence of many PAC/PVC episodes interspersed with NSR can mimic the random dynamics of the AF.

There is a need to enhance the real-time realizable AF algorithm for accurate detection of, and discrimination between, NSR, AF, PVC, and PAC.

BRIEF SUMMARY

Enhanced real-time realizable AF algorithm for accurate detection of, and discrimination between, NSR, AF, PVC, and PAC are disclosed herein below.

In one or more other embodiments, a real-time arrhythmia discrimination method is used in smartphones, which can discriminate between NSR, AF, PACs and PVCs using pulsatile time series collected from a smartphone's camera. To increase the sensitivity of AF detection and add the new capabilities of PVC and PAC identification, the arrhythmia discrimination method of these teachings combines Root Mean Square of Successive RR Differences (RMSSD), Shannon Entropy (ShE) and turning point ratio (TPR), used in the previous AF detection algorithms, with the Poincare plot, and utilizes the features of pulse rise/fall time and amplitude for arrhythmia discrimination. The RMSSD, ShE, Poincare plot and pulse rise/fall time and amplitude features have been widely used in analyzing heart rhythms while the TPR was proposed to be applied to heart rhythm analysis. In one instance, the conventional Poincare plot (or TPR) is modified I is him and him and him him him him him and him and him and him to discriminate bigeminy, trigeminy and quadrigeminy patterns of PACs/PVCs as well as detect PAC/PVC rhythms themselves among non-NSR subjects. Moreover, the use of pulse rise/fall times and amplitudes is especially well-suited for differentiating between the PAC and PVC.

For a better understanding of the present teachings, together with other and further objects thereof, reference is made to the accompanying drawings and detailed description and its scope will be pointed out in the appended claims.

DETAILED DESCRIPTION

Figure 1:
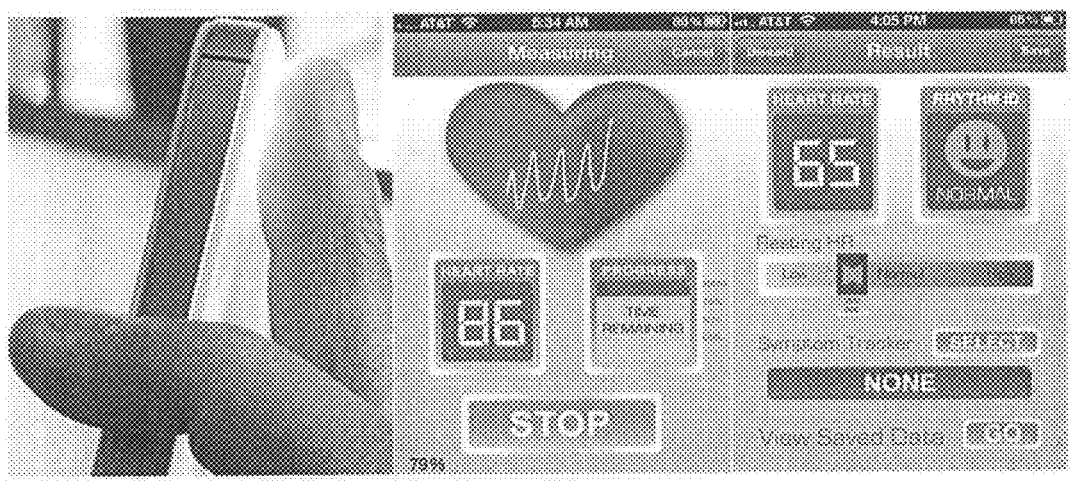
FIG. 1 represents a smart phone application for data recording (the application uses the camera lens and illumination to acquire information about heart rate and rhythm.

The following detailed description presents the currently contemplated modes of carrying out the invention. The description is not to be taken in a limiting sense, but is made merely for the purpose of illustrating the general principles of the invention, since the scope of the invention is best defined by the appended claims.

Current AF algorithms: A number of algorithms have been developed to detect AF and can be categorized as being based on 1) P-wave detection or 2) RR interval (RRI) variability. Since there is no uniform depolarization of the atria during AF, there is no discernible P-wave in the ECG. This fact has been utilized in detection of AF by trying to identify whether the P-wave is absent. However, in most cases the location of the P-wave fiducial point is very difficult to find and often corrupted by noise that is inherent in surface measurements. The methods in the second category do not require identification of the P-wave and are based on the variability of RRI series. However, few algorithms in this category show high predictive value for clinical application. A notable exception includes an algorithm which compares the density histogram of the test RRI (and $\Delta RRI$) segment with previously-compiled standard density histograms of RR (and $\Delta RR$) segments during AF using the Kolmogorov-Smirnov test. The inventors reported a sensitivity of 94.4% and specificity of 97.2% for AF beats in the MIT-BIH AF database. Similar accuracy was reported by Sarkar et al. using a Lorenz plot between $\Delta RR(i-1)$ and $\Delta RR(i)$, which is incorporated into the Reveal XT product. It should be noted that the accuracy of these 2 methods rely on the robustness of the training data. An AF detection algorithm based on statistical analysis of RRI has been recently developed and has been found to produce similar accuracy (see also US Patent application Publication 20110166466, "R INTERVAL MONITORING METHOD AND BLOOD PRESSURE CUFF UTILIZING SAME," issued as U.S. Pat. No. 8,417,326, and WIPO Publication of International Application No.: PCT/US12/66626, TIME-VARYING COHERENCE FUNCTION FOR ATRIAL FIBRILLATION DETECTION, and corresponding US Patent Application Publication 2013-0144180, all of which are Incorporated by reference herein in its entirety and for all purposes). The main advantage of that approach is that it is computationally fast (<0.08 ms per 2 minutes of data) and requires storage of only 3 threshold values. Note that the algorithms by Tateno and Glass, and Sarkar et al., require storage of large amounts of histogram data and threshold values of various characteristics of AF. Importantly, none of the AF detection algorithm described herein above has been proven capable of diagnosing AF and differentiating AF from PAC and PVC or of doing so using standard smartphone technologies (memory, processor, illumination, and camera).

Current PVC and PAC algorithms: From an algorithmic development perspective, automatic detection of PVCs and PACs is difficult because premature beats often occur infrequently and can be random, leading to false positive AF detection. Premature atrial contractions are generated when a region of the atria other than the sinoatrial node fires early, leading to premature activation of the atria and ventricles. Although spontaneous left atrial/pulmonary vein activity has been shown to trigger AF in some individuals, the link between PACs and risk for AF remains unclear. Premature ventricular contractions occur when a region below the atrioventricular node spontaneously depolarizes, leading to ventricular activation. Both PACs and PVCs can cause symptoms of palpitations very similar to AF, but, as opposed to AF, the clinical course of affected patients is typically benign. Last, PACs and PVCs occur in patterns, specifically occurring every 2nd, 3rd, or 4th beat, termed bigeminy, trigeminy, and quadrigeminy, or combinations of the three.

The presence of many PAC and PVC episodes interspersed among NSR can alter the cardiac signal's dynamics, even mimicking the characteristics of AF. This is because the presence of either PAC or PVC increases the variability in the pulse interval, resulting in more random-like behavior than a segment of data with only NSR. It has been observed that in a 60-beat segment, three or more episodes of PVC, PAC or a combination of the two does result in incorrect detection of AF using an AF detection algorithm. In some patients, therefore, the prevalence of PAC/PVC causes false detection of AF using AF detection algorithm as shown in the Preliminary Results section. Hence, there is a need for developing a new algorithm for detection of PAC/PVC from a pulse interval signal derived from a smartphone.

The most widely-used algorithm for PAC and PVC detection from an ECG signal is based on template matching of PAC/PVC episodes. The main limitation of this approach is that many templates of PAC/PVC waveforms need to be stored in memory and they are compared beat-by-beat to the ECG signal. This approach is clearly only suited for offline computer analysis, not for applications for real time analysis, such as, but not limited to, smartphone applications. These teachings consider a real-time realizable and more efficient method for detection of PAC/PVC than the template matching approach.

The AF Detection Algorithm of (8)

As stated in Dash S, Chon K H, Lu S, Raeder E A, Automatic real time detection of atrial fibrillation. Ann Biomed Eng. 2009: 37(9): 1701-9, the algorithm includes:

AF Detection Algorithm:

Step 1: Root Mean Square of Successive Differences (RMSSD) was calculated using the following formula:

$$RMSSD = \left( \frac{1}{l-1} \sum_{j=1}^{l-1} (a(j+1) - a(j))^2 \right)^{\frac{1}{2}} \quad (1)$$

We divide the RMSSD value by the mean RRI in order to account for the beat-beat variations in HR. This ratio is then compared to a threshold (RmsThresh).

Step 2: Turning Point Ratio (TPR) is based on the nonparametric "Runs Test" used to measure the degree of randomness in a particular time-series. Each beat in a RRI segment is compared to its 2 nearest neighbors and is designated a Turning Point (TP) if it is greater or less than both. The expected number of TP's in a segment of length 1 is given by $$\mu_{TP} = \frac{2l-4}{3} \quad (2)$$

$$\sigma_{TP} = \sqrt{\frac{16l-29}{90}} \quad (3)$$

A beat segment is considered random if the number of turning points (or TPR, if it is normalized against the length. 1) falls within some threshold confidence interval (TprThresh) of the expected TPR.

Step 3: Shannon Entropy (SE) is a metric used to measure the level of uncertainty in a random variable by quantifying the probability that runs of patterns exhibiting regularity over some duration of data exhibit similar patters over the next duration of data. It is calculated, from a histogram of RR intervals in a segment of length 1 using 16 equally spaced bins. We can define a probability distribution for the RRI segment using;

$$p(i) = \frac{N_{bin(i)}}{l - N_{outliers}} \quad (4)$$

Here, $N_{bin(i)}$ is the number of beats in the ith bin and $N_{outlier}$ is the number of outliers (16 in or case) and p(t) is the probability associated with all beats falling in the ith bin. The SE is then calculated as $$SE = -\sum_{i=1}^{16} \frac{p(i)\log(p(i))}{\log\left(\frac{1}{16}\right)} \quad (5)$$

The SE is compared to a threshold (SeThresh) to be derived after tuning using the ROC curve.

Step 4: After all the above statistics are calculated, a simple AND condition is applied. The heat segment Is considered AF only if all the above statistics cross their respective thresholds.

Motion and noise artifact detection algorithms: Clinicians have cited motion and noise artifacts in ambulatory monitoring devices as the most common cause of false positive arrhythmia detection, loss of key electrocardiographic data, and inaccurate readings. Numerous efforts have been made, but motion and noise artifacts remain a key obstacle to accurate detection of arrhythmias, including AF, PVC and PAC. A method to separate clean ECG and pulse oximeter segments from segments with motion and noise artifacts in real time has been developed, thereby increasing the specificity of the identification of AF, PVC and PAC from NSR (see PCI Published Application WO 2012/051320, corresponding to WiPO (PCT) International Application Number PCT/US11/55989, filed on Oct. 12, 2011, entitled MOTION AND NOISE ARTIFACT DETECTION FOR ECG DATA, and PCT Publication No. WO 2012/051300, corresponding to PCT/US2011/055966, filed on Oct. 12, 2011, both of which are incorporated by reference herein in their entirety and for all purposes). Health monitoring using a smartphone is a nascent area, hence, there is scant literature on motion and noise artifact detection algorithms that are specific to mobile health monitoring. The Results section details various approaches that have been already implemented with the AF detection application to reduce motion and noise artifacts so that false positive detection of AF are minimized.

NSR, AF, PVC, and PAC Databases and Clinical Data Collection

For the iPhone data collection, 88 subjects with recordings were obtained before and after cardioversion, as well as 7 with PACs and 4 with PVCs were recruited at UMMC. The subjects all gave their informed consent (H#14490) (IRB numbers for the studies). Participants were Instructed to place their first (index) or second (middle) finger on a standard smart phone camera with the flash turned on. (the flash will be automatically invoked by the application software) for two minutes. Data were recorded with participants in a supine position with spontaneous breathing. FIG. 1 shows a current prototype of arrhythmia discrimination application for iPhone 4S.

Preprocessing

Videos of their fingertip blood flow intensity were taken with 640×480 pixel resolution at a sampling rate of 30 frames per second and processed in real time. Only the green band from the RGB video was used as recent results indicate this gives the best signal fidelity. An average is made of the intensity values of the upper 320×480 pixels in each frame, i.e. the upper half of the fingertip on the green video signal, as our systematic analysis showed this region provided the best signal quality. Once the clean green signals are identified, pulse beat-to-beat detection from the green signals was performed incorporating interpolation, sudden DC change elimination, two stages of band pass filter, derivative rank filter and snatching of original peaks.

Arrhythmia Discrimination

Figure 2A:
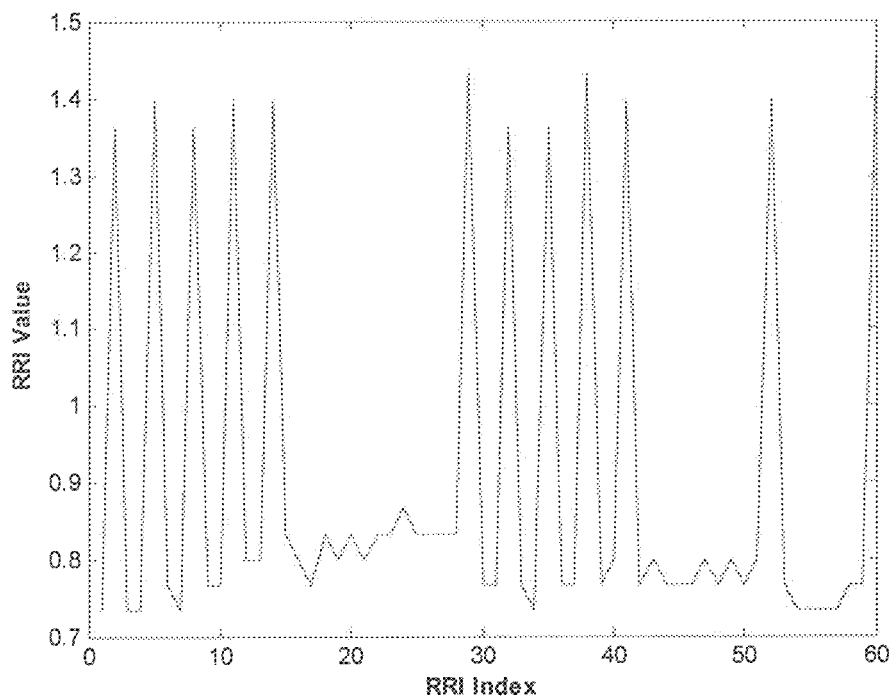
FIGS. 2a-2c show Three PPI sequences extracted from 60 beat-to-beat segments.
Figure 2B:
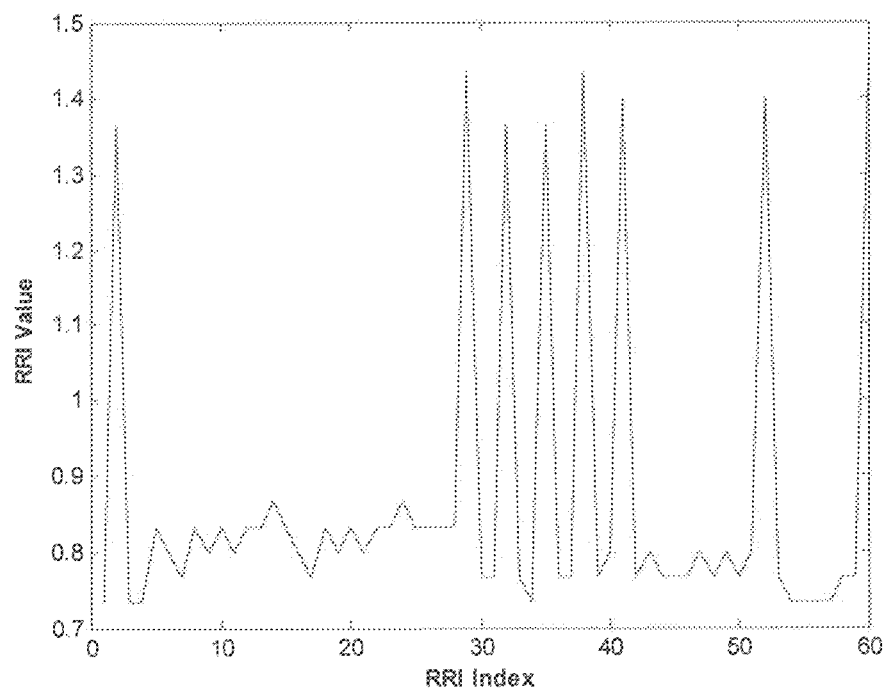
Figure 2C:
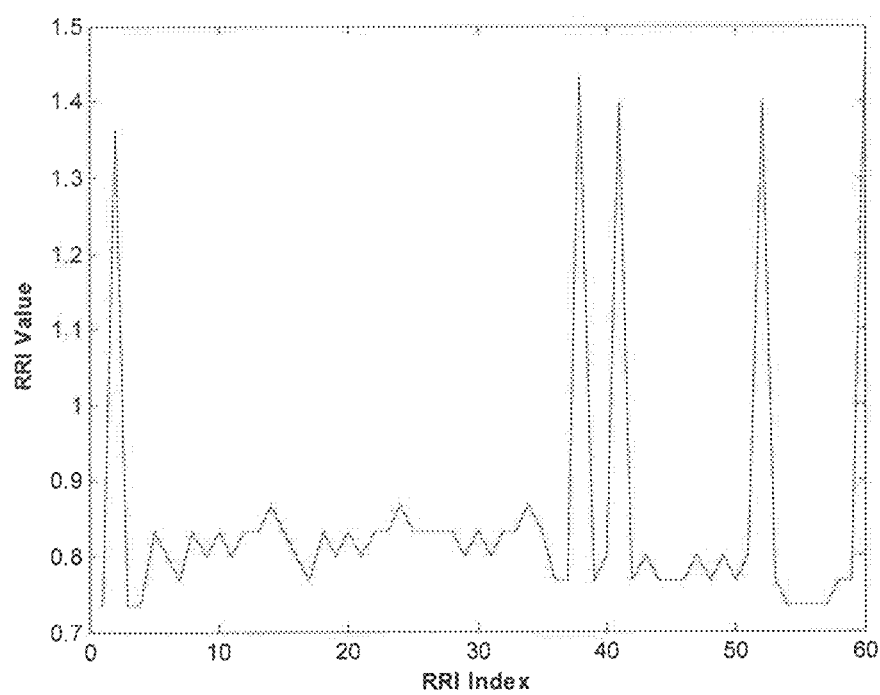
Figure 3:
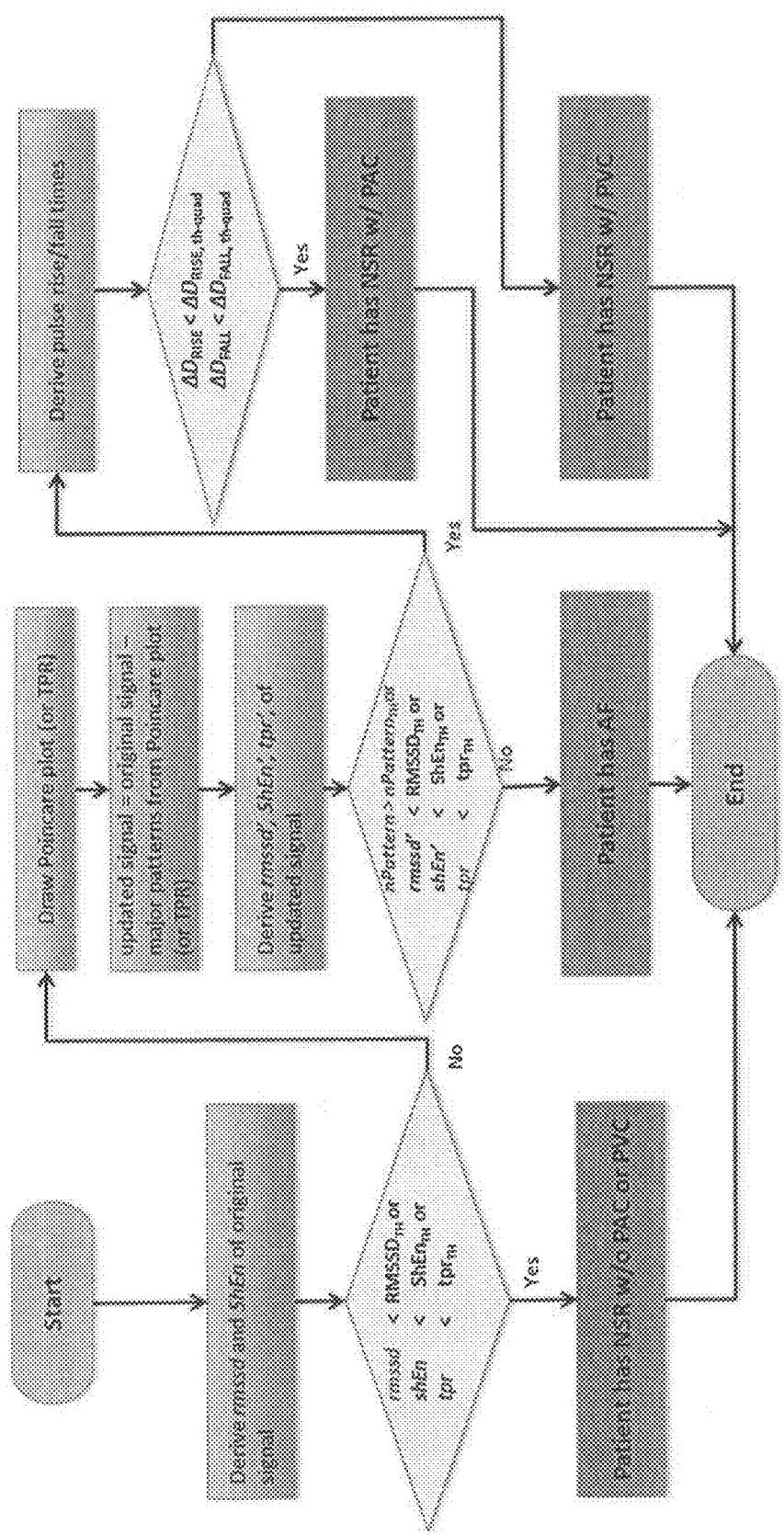
FIG. 3 is a Flowchart of NSR, AF, PVC, PAC detection and discrimination procedures.

FIG. 2(a)-(c) shows three cases of PPI sequences of 60 beat-to-beat segments with ten, six, and three PAC quadrigeminy patterns, respectively. The previous algorithm which is based on RMSSD and ShE classifies 60 beat-to-beat segments with at least 4 PAC patterns to be AF (see FIGS. 2(a) and 2(b)) while classifying those with less than 4 PAC patterns to be NSR (see FIG. 2(c)). The method of these teachings includes PAC and PVC discrimination capability which will further improve AF detection accuracy. The proposed arrhythmia discrimination algorithm is detailed in a flowchart, which is shown in FIG. 3.

Feature Extraction

Figure 4:
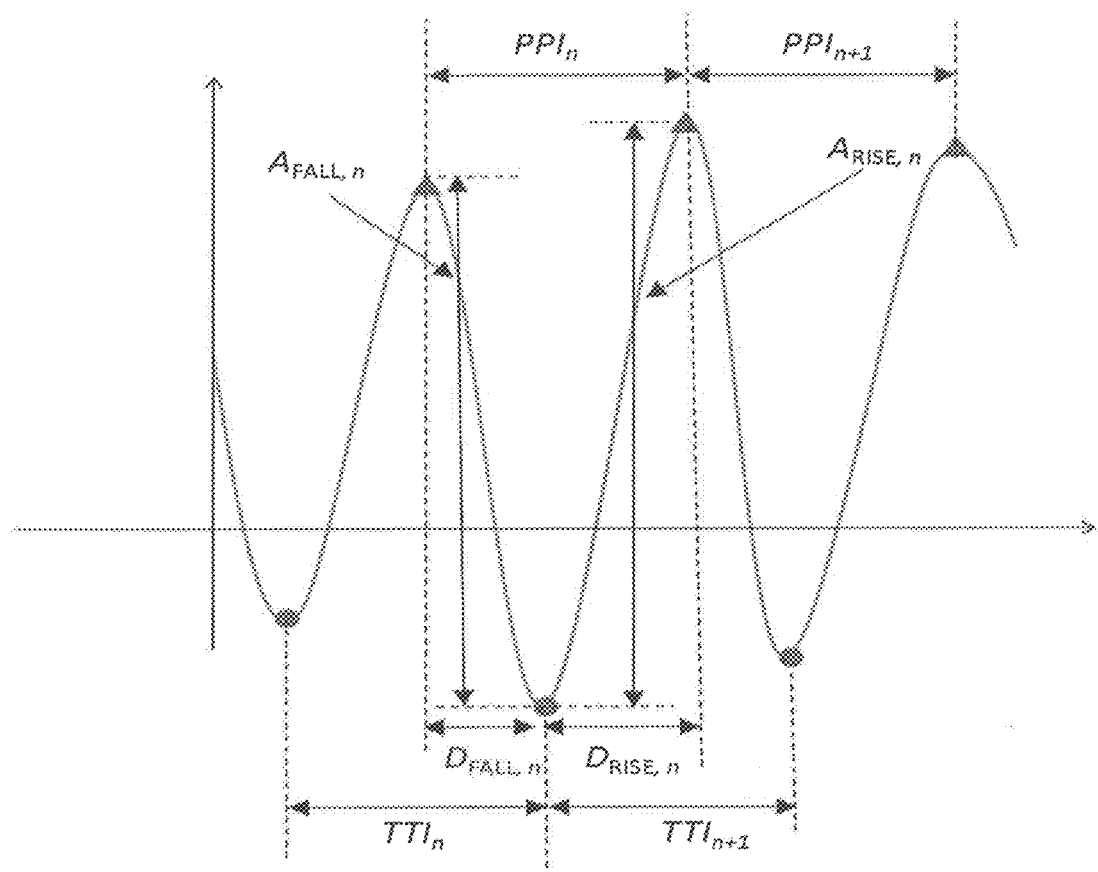
FIG. 4 shows Feature extraction of smartphone pulsatile time series. PPI and TTI are used to discriminate between AF, PAC/PVC and NSR as well as identify specific patterns (bigeminy, trigeminy, and quadrigeminy) of PAC/PVC. $D_{RISE}$, $D_{FALL}$, $A_{RISE}$, and $A_{FALL}$ are for differentiating between PAC and PVC.

In one instance, the method of these teachings extracts features of the PPI signal, e.g., peak-to-peak interval (PPI) and trough-to-trough interval (TTI), rise time ($D_{RISE}$) and fall time ($D_{FALL}$) from the measured pulsatile time series. As shown in FIG. 4, the PPI is calculated by the difference between two successive peak times, $T_{PEAK,n}-T_{PEAK,n-1}$, and TTI is obtained by the difference between two successive trough times, $T_{TROUGH,n}-T_{TROUGH,n-1}$. $D_{RISE}$ is defined by the difference between the peak and the trough of the $n^{th}$ pulse, $T_{PEAK,n}-T_{TROUGH,n}$ while $D_{FALL}$ is the difference between the trough of the $n^{th}$ pulse and the peak of the $n-1^{th}$ pulse and, $T_{TROUGH,n}-T_{PEAK,n-1}$. Similarly, $A_{RISE}$ is $Y_{PEAK,n}-Y_{TROUGH,n}$ while $A_{FALL}$ is $Y_{PEAK,n-1}-Y_{TROUGH,n}$.

NSR Discrimination from AF, PAC and PVC Subjects Using RMSSD and ShE

First, the RMSSD and ShE are derived from the PPI. The RMSSD is to measure the variability in a time series sequence and is calculated as follows:

$$RMSSD(a_i, K, a_{i+L-1}) = \sqrt{\frac{1}{L}\sum_{j=0}^{L-1}\{a_{i+j} - a_{i+j-1}\}^2} \quad (1)$$

The RMSSD of NSR is expected to be small compared to those of AF, PAC and PVC, The ShE is to quantify the regularity of pattern in a time series and ShE on the time series $a_i, K, a_{i+L-1}$ is derived as $$ShE(a_i, K, a_{i+L-1}) = -\sum_{k=1}^{N_{BIN}} \frac{p(a_i, K, a_{i+L-1}, k)\log p(a_i, K, a_{i+L-1}, k)}{\log(1/N_{BIN})} \quad (2)$$

where $N_{BIN}$ denotes the number of bins, of which each has lower ($B_{LOW,k}$) and upper ($B_{UP,k}$) bin boundaries for $k \in \{1, N_{BIN}\}$ and $p(a_i, K, a_{i+L-1}, k)$ is expressed as:

$$p(a_i, K, a_{i+L-1}, k) = \sum_{j=0}^{L-1} U(a_{i+j}, k)/(L - N_{outliers}) \text{ for } U(a_{i+j}, k) = \begin{cases} 1, & B_{LOW,k} < a_{i+j} < B_{UP,k} \\ 0, & \text{otherwise} \end{cases}$$

The ShE of NSR Is expected to be small compared to those of AF, PAC and PVC. The TPR is to measure a degree of independence in a time-series. A turning point (TP) is defined as a point having larger or smaller value than two nearest neighbor points. The TPRs of NSR and AF are expected to be within in a range since they are from random RRIs while those of PAC and PVC axe expected to be out of the range due to their regularities.

The method of these teachings compares the RMSSD, ShE and TPR of PPI to their corresponding thresholds, respectively. If both of them are less than their thresholds, the pulsatile time series is classified as NSR without PAC or PVC (see the first condition in the flowchart in FIG. 3. Otherwise, the algorithms goes to next step and checks if the pulsatile time series is AF or PAC/PVC.

PAC/PVC Discrimination from non-NSR subjects using Poincare Plot or TPR

Our discrimination algorithm uses Poincare plot or TPR to determine if the non-NSR subject has PAC/PVC interspersed with NSR. Moreover, the algorithm gives information of PAC/PVC patterns, e.g., bigeminy, trigeminy, and quadrigeminy.

Poincare Plot

Figure 5:
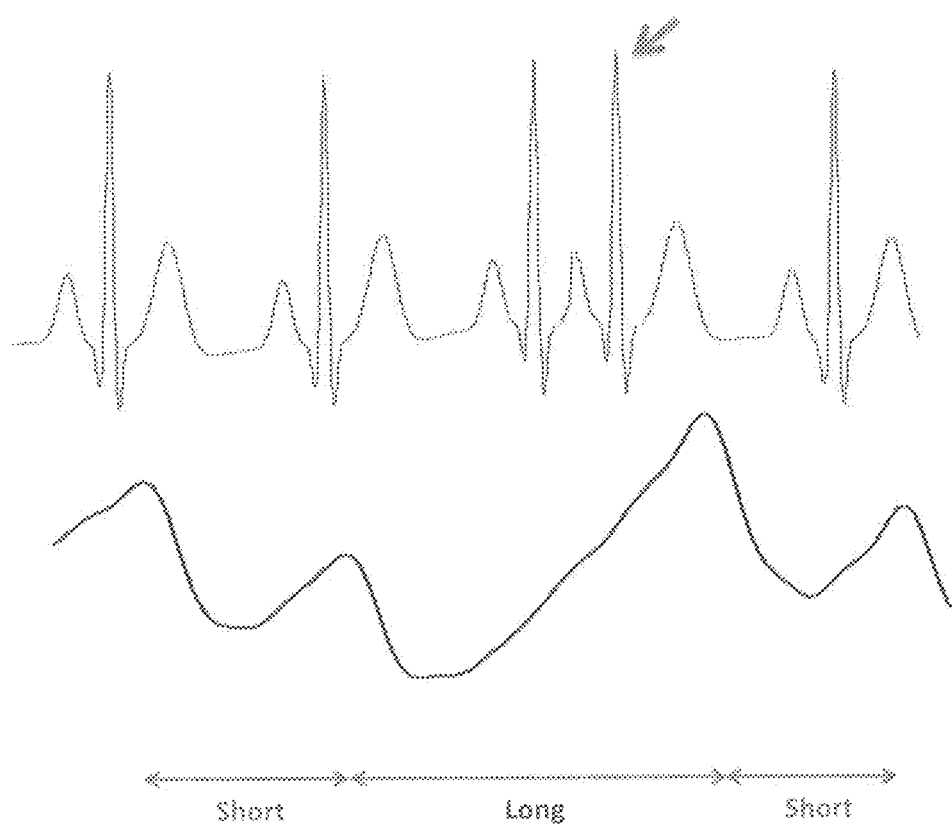
FIG. 5 depicts a Comparison of ECG RR intervals to pulse intervals obtained from an iPhone in a PAC episode (a premature atrial contraction results in a longer duration pulse interval and larger amplitude pulse beat when compared to a normal pulse heat)

Shown at the bottom panel of FIG. 5 is an iPhone recording of a PAC subject and the top panel represents Its corresponding ECG data. When a PAC episode occurs as noted by an arrow on the top panel of FIG. 5, the rising phase of iPhone's PPI recording is markedly prolonged. Hence, taking the difference between the iPhone peak times of a normal beat and a PAC beat following another normal beat (ΔPPI), a "long" pulse interval is obtained (noted by a red interval). The difference between two consecutive normal, pulse beats Is termed the "short" pulse interval. The occurrences of PAC and PVC episode at every 2nd, 3rd and 4th pulse beats are known as bigeminy, trigeminy and quadrigeminy, respectively. We adopt a Poincare plot, which is widely used to quantify the similarity in time series $x_i$ for $i=2 \ldots, N$ by drawing a two-dimensional plot $(x_{i-1}, x_i)$, to characterize ΔPPI dynamics and to discriminate PAC/PVC episodes from those of AF and NSR (see, for example, Sarkar S, Ritscher D, Mehra R. A detector for a chronic implantable atrial tachyarrhythmia monitor. IEEE Trans Biomed Eng, 2008; 55(3):1219-24, which is Incorporated by reference herein is entirety and for all purposes).

Figure 6:
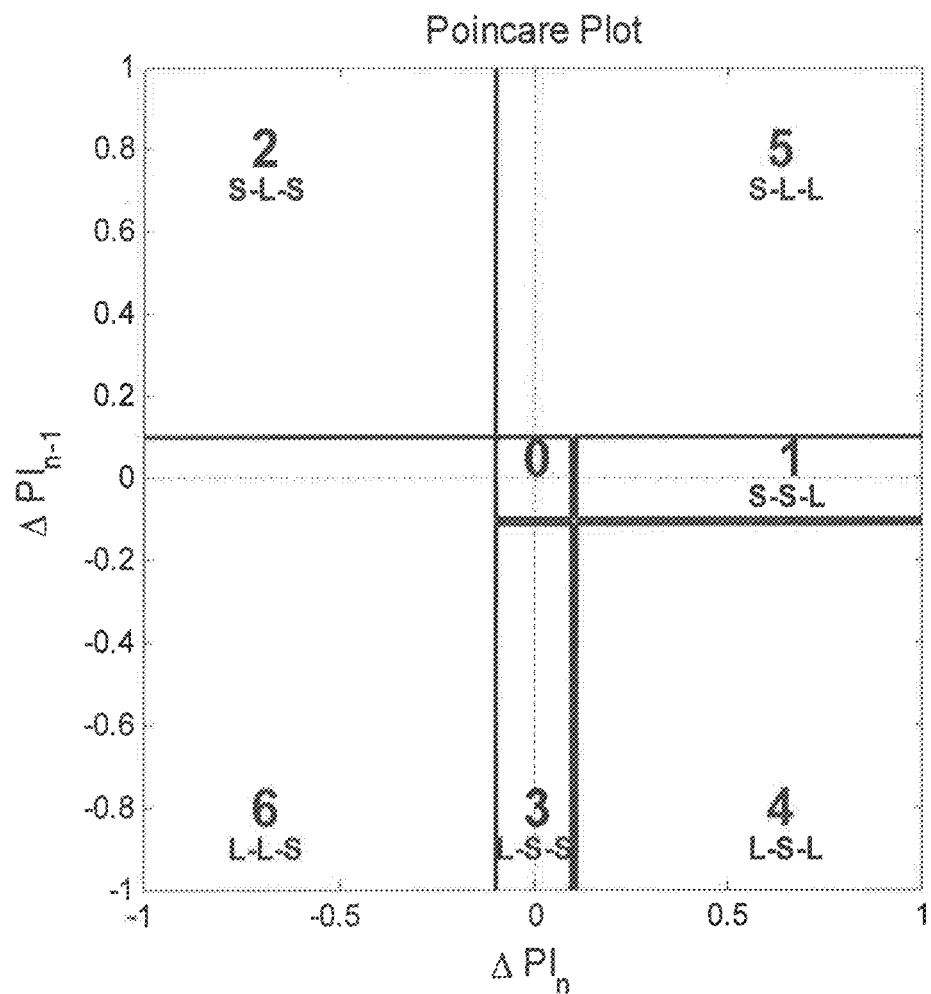
FIG. 6 is Poincare plot divided into six regions. AF, NSR, PVC and PAC rhythms will have different trajectory patterns and they may be confined to only a single region or multiple regions as demonstrated in FIG. 4.

To facilitate the discrimination among bigeminy, trigeminy and quadrigeminy patterns of the PAC and PVC, the Poincare plot was divided into six regions as shown in FIG. 6. The six regions represent permutations of all possible sequences of "long" and "short" based on 3 consecutive pulse intervals which are derived, from 4 consecutive pulse beats as detailed in Table I. The region boundary was set optimally based on experiment results. The Poincare plot trajectory patterns of NSR, AF, PAC and PVC are respectively detailed in Table II

TABLE I

POINCARE PLOT SECTORS CORRESPONDING TO PAC/PVC PATTERNS WHICH CONSIST OF BIGEMINY, TRIGEMINY AND QUADRIGEMINY.

| $PI_{i-2}$-$PI_{i-1}$-$PI_i$ | Region $ID_i$ |
|---|---|
| Short-Short-Long | 1 |
| Short-Long-Short | 2 |
| Long-Short-Short | 3 |
| Short-Short-Short | 0 |
| Long-Long-Long | 0 |
| Long-Long-Short | 4 |
| Short-Long-Long | 5 |
| Long-Short-Long | 6 |

TABLE II

ARRHYTHMIA WITH ITS CORRESPONDING TRAJECTORY PATTERN IN POINCARE PLOT

| Type of Arrhythmia | Trajectory Patterns in the Poincare plot's six regions($\Delta PI_{i-1}$, $\Delta PI_i$) |
|---|---|
| Premature Atrial Contraction (PAC) | |
| Bigeminy | 0-0-0-0-0-0- . . . |
| Trigeminy | 2-4-2-4-2-4- . . . |
| Quadrigeminy | 1-2-3-1-2-3- . . . |
| Premature Ventricular Contraction (PVC) | |
| Bigeminy | 0-0-0-0-0-0- . . . |
| Trigeminy | 2-4-2-4-2-4- . . . |
| Quadrigeminy | 1-2-3-1-2-3- . . . |
| Normal Sinus Rhythm (NSR) | 0-0-0-0-0-0- . . . |
| Atrial Fibrillation (AF) | irregular patterns with trajectories at all 6 possible regions |

Moreover, the PAC and PVC are further classified into bigeminy, trigeminy, and quadragemiuy patterns. Note that the trajectory pattern associated with NSR is expected to be "0-0-0-0-0-0- . . . " while AF is irregular at all 6 possible regions. Moreover, the various combinations of trigeminy and quadrigeminy associated with the PAC or PVC are distinct from either the NSR or AF. Combinations of PAC and PVC patterns have more orderly patterns (since the phase trajectory patterns will largely be confined to regions 0, 1, 2, 3 and 4 as shown above) than the random trajectory patterns associated with AF (trajectory patterns are evident in all regions of the Poincare plot). For bigeminy rhythm, the difference between NSR and PAC/PVC bigeminy is that the bigeminy has larger PPI value than NSR. Hence, the PAC/PVC bigeminy can be appropriately discriminated by the mean and variance.

Turning Point Ratio (TPR)

To apply TPR in discriminating PAC/PVCs, we redefine a TP as a point where a specific pattern starts, e.g. bigeminy, trigeminy and quadrigeminy patterns. If an unknown time series has similar number of TP (or TPR), related to a specific pattern, to that of an independent time series, the unknown series is expected to be independent. Otherwise, the time series is expected to be dependent.

To detect a quadrigeminy, we define $TP_{QUAD}$ as a starting point of "Short-Short-Long-Short-Short-Long-Short-Short (SSLSSLSS)" in a PPI sequence. Considering an independent time sequence $x_i$, the probability of a point being quadrigeminy TP is given by:

$$Pr\{X_{i-2} < X_i, X_{i-1} < X_i, X_i > X_{i+1}, X_i > X_{i+2},$$
$$X_{i+3} > X_{i+1}, X_{i+3} > X_{i+2}, X_{i+3} > X_{i+4}, X_{i+3} > X_{i+5}\} =$$
$$\int_{x=-\infty}^{\infty} Pr(x > X_{i-1})Pr(x > X_{i-2})Pr(x > X_{i+1}, x > X_{i+2}, X_{i+1} < X_{i+3},$$
$$X_{i+2} < X_{i+3}, X_{i+4} < X_{i+3}, X_{i+5} < X_{i+3})f(x)dx =$$
$$\int_{x=-\infty}^{\infty} \left\{\frac{1}{3}F(x)^4 - \frac{F(x)^7}{30}\right\}f(x)dx = \frac{1}{16}$$

Using the stochastic theory, the expectation $\mu_{TP,quad}$ and standard deviation $\rho_{TP,quad}$ of the number of quadrigeminy TPs in a segment i are given by $$\mu_{TP,QUAD} = \frac{l-7}{16}, \sigma_{TP,QUAD} \approx \sqrt{0.0601\,l - 0.4255}$$

Figure 7A:
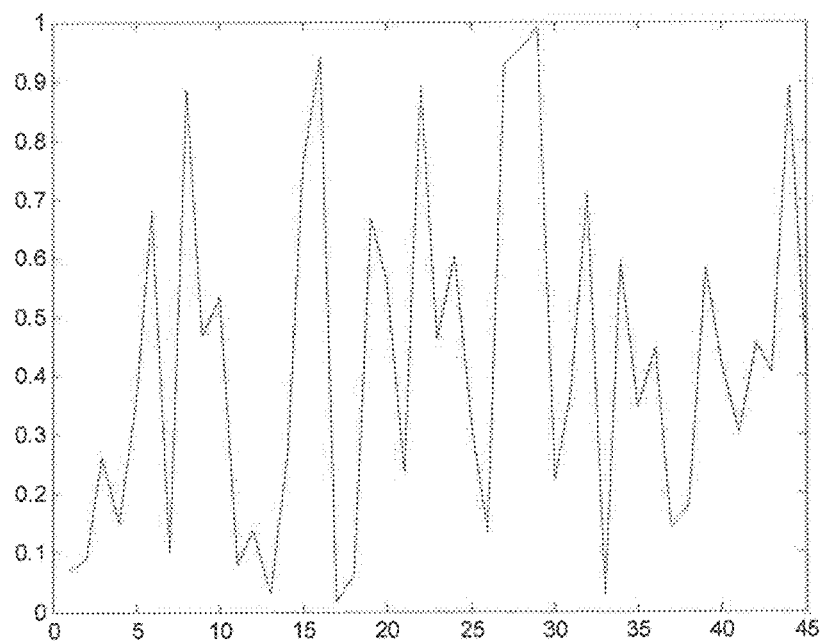
FIGS. 7a-7b show TPR of Independent and dependent processes, (a): Independent process-random (TPR=0.0), (b): dependent process-PAC-quadrigeminy (TPR=0.125)
Figure 7B:
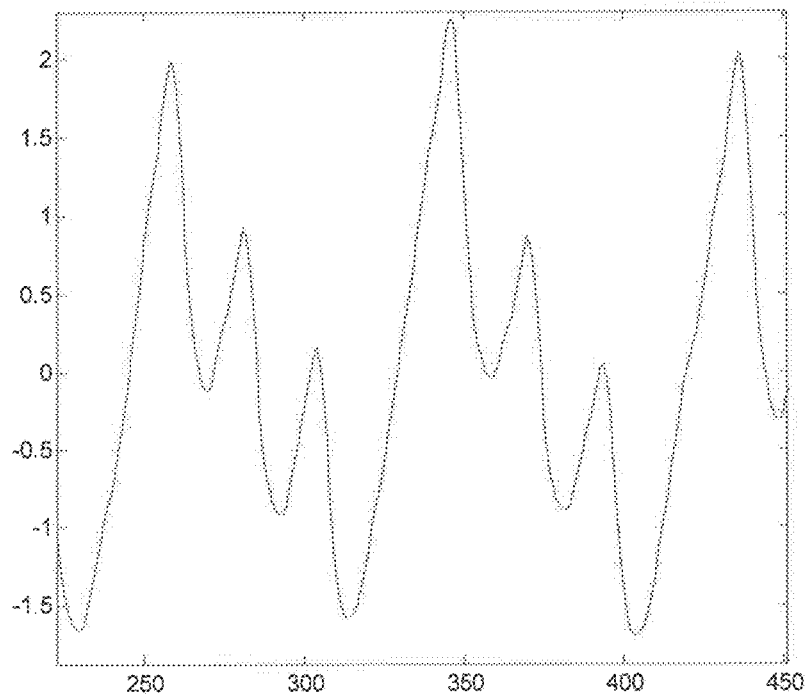

For example, an independent pulsatile time series with i=45 has $\mu_{TP,QUAD}$ and of $\rho_{TP,QUAD}$ of 1.435 and 1.737, respectively. A PPG segment is considered independent if the number of TPs (or TPR) falls within some threshold confidence interval TpThresh (or TprThresh) of the expected TP (or TPR). Otherwise, a PPG segment is not considered to be dependent. For example, the TPR method determines FIGS. 7(a) and 7(b) to be non-quadrigeminy and quadrigeminy, respectively.

For trigeminy, we defined the $TP_{TRI}$ as a starting point where "Short-Long-Short-Long-Short (SLSLS)" PPI pattern begins. Hence, the probability of being $TP_{TRI}$ is similarly givers by:

$$Pr\{X_{i-1} < X_i > X_{i+1} < X_{i+2} > X_{i+3}\} =$$
$$\int_{-\infty}^{\infty} Pr\{X_{i-1} < x\}Pr\{x > X_{i+1} < X_{i+2} > X_{i+3}\}f(x)dx =$$
$$\int_{-\infty}^{\infty} \left(\frac{F(x)^2}{2} - \frac{F(x)^4}{6}\right)f(x)dx = \frac{2}{15}$$

The $\mu_{TP,TRI}$ and $\rho_{TP,TRI}$ are given by:

$$\mu_{TP,TRI} = \frac{2(l-4)}{15}, \sigma_{TP,TRI} \approx \sqrt{0.0826\,l - 0.2527}$$

For bigeminy, TPs are defined as a starting point where "Long-Long (LL)" PPI pattern starts. PAC/PVC bigeminy is appropriately discriminated by the mean and variance than TPR since the TPR of PAC/PVC is expected to be similar to that of NSR.

Differentiation Between PVC and PAC Using Pulse Amplitude and Rise/Fall Times

The PVC and PAC have similar Poincare plot trajectories and TPR values for the same pattern type (bigeminy, trigeminy, and quadrigeminy). To discriminate between PAC and PVC, our arrhythmia discrimination algorithm utilizes the physiological difference between PAC and PVC explained in the followings.

Figure 8A:
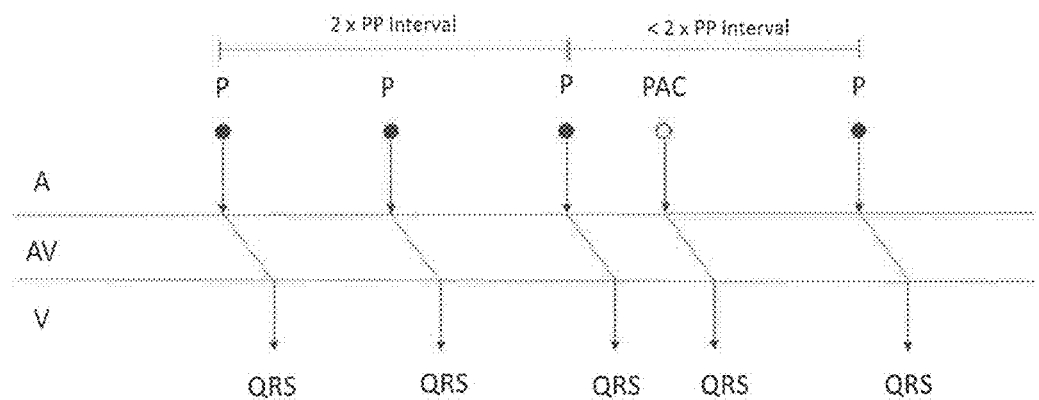
FIGS. 8a-8b show Heart rhythm timing diagrams of representative (a) PAC and (b) PVC subjects. PAC and PVC episodes are interspersed with NSR episodes. (a): incomplete compensatory pause is occurred between the PAC episode and the fourth NSR episode, and (b): complete compensatory pause is occurred between the PVC episode and the fourth NSR episode.
Figure 8B:
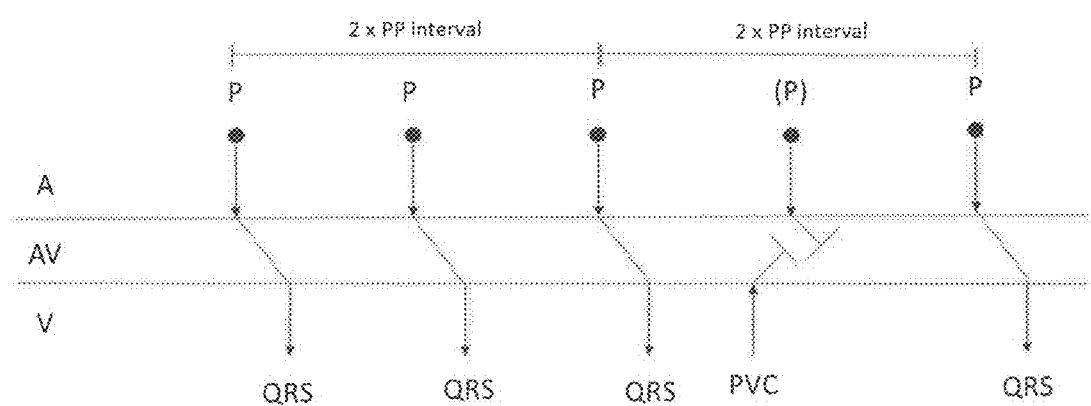

A PAC is an abnormal beat initiated in the atria before sinoatrial (SA) node triggers and the PAC usually interrupts the SA node and resets its timing. Hence, the PAC mostly generates a QRS complex similar to the NSR episode. Moreover, the NSR episode following a PAC usually occurs at time rescheduled by the PAC (called incomplete compensatory pause) as shown in FIG. 8(a). On the other hand, a PVC is a beat initiated in the ventricle before atrioventricular (AV) node triggers and the PVC does not usually interrupt the SA node. Hence, the NSR episode following a PVC usually occurs at previously scheduled time by SA node (called complete compensatory pause) as shown in FIG. 8(b). Moreover, the PVC usually generates a wider QRS complex compared to that of an NSR episode.

The completeness/incompleteness is distinguished by the rise/fall times of the pulse signals. PAC episodes are usually expected to have similar rise/fall times similar to those of NSRs while PVC episodes have different fall times compared to those of NSRs. We define the difference ($\Delta D_{RISE}$) between the rise times of current and previous beats, i.e., $\Delta D_{RISE} = D_{RISE,n} - D_{RISE,n-1}$. Similarly, we define the difference between the fall times as $\Delta D_{FALL,n} = D_{FALL,n} - D_{FALL,n-1}$. For the ectopic beat of n, we derive the rise/fall time differences between ectopic beat and a normal beat following the ectopic beat which are $\Delta D_{RISE,n+2}$ and $\Delta D_{FALL,n+2}$, respectively. If $\Delta D_{RISE,n+2}$ and $\Delta D_{FALL,n+2}$ are within $\Delta D_{RISE,th\text{-}quad}$ and $\Delta D_{FALL,th\text{-}quad}$, the ectopic beat is determined to be a PAC. Otherwise, it is considered as a PVC. For trigeminy beat of n, we utilize the differences between peak times between a normal before an ectopic beat and another normal beat after the ectopic beat, i.e., $\Delta PPI_{n+1} = PPI_{n+1} - PPI_n$. If the difference is less than $\Delta PPI_{th\text{-}tri}$, the ectopic beat is determined to be a PAC. Otherwise, the beat is considered as a PAC.

Results

The performance of the arrhythmia discrimination algorithm was evaluated with iPhone's pulsatile time series data. Two minute pulsatile time series is collected from each subject. We compared our new algorithm to the previous arrhythmia discrimination algorithms, which are based on RMSSD and ShE. As performance metrics, we considered classification accuracy, sensitivity and specificity.

Detection of NSR

Figure 9:
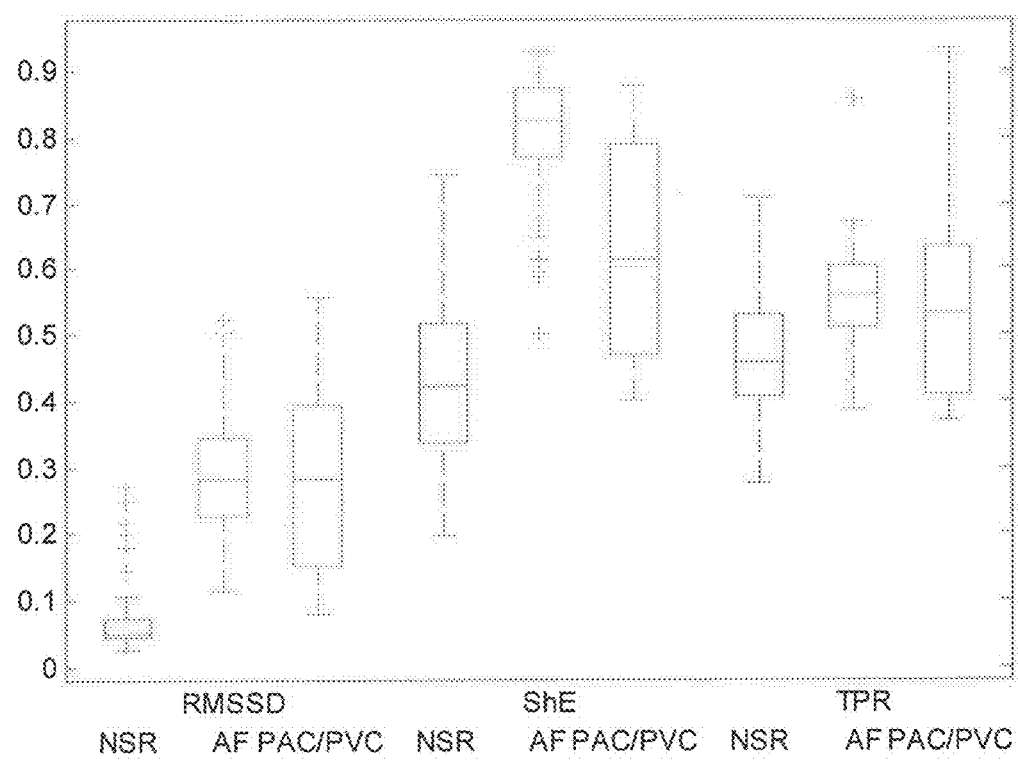
FIG. 9 shows a comparison of statistical values (RMSSD, ShE and TPR) between NSR, AF and PAC/PVC; the central mark on each box corresponds to the median; the edges of the box correspond to the 25th and 75th percentiles, the whiskers extend to the most extreme data points not considered outliers, and outliers are plotted individually.

FIG. 9 compares the RMSSD (left), ShE (middle) and TPR. (right) values of NSR, AF and PAC/PVC subjects. We performed paired t-test to determine if there are significant RMSSD differences between NSR, AF and PAC/PVC. The p-values between NSR and each arrhythmia indicate that RMSSD values are significantly different (p<0.05 at 95% CI) between NSR and each of other arrhythmias. However. RMSSD differences between AF and PAC/PVC are not significant. Similarly, ShE and TPR values of NSR, AF and PAC/PVC subjects are also found significantly different between NSR and each of arrhythmia, respectively. Based on this observation, we applied RMSSD, ShE and TPR thresholds to classifying NSR subjects from others rhythms. The optimal RMSSD and ShE threshold values are derived as 0.09275, 0.3800 and 0.3600, respectively. As a result, the proposed method detects NSR with accuracy of 0.9788 which is higher than accuracy of 0.9577 from the conventional algorithm based on a combination of Rmssd and ShE.

PAC/PVC Discrimination among non-NSR Subjects: Poincare Plot vs. TPR

Poincare Plot

Figure 10A:
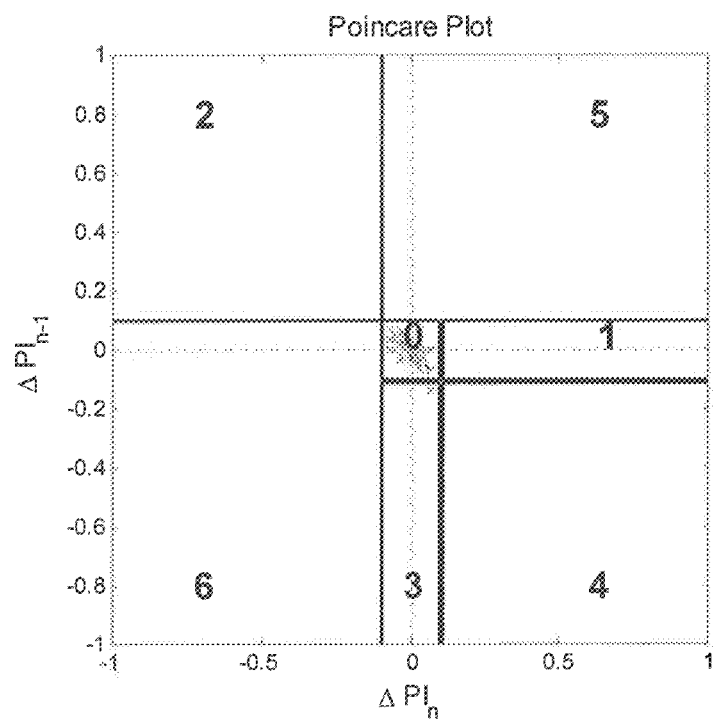
FIGS. 10a-10d are Poincare plots with ($\Delta PI_{j-1}$, $\Delta PI_1$) trajectory, (a): NSR: (b): AF, (c): PVC-quadrigeminy, (d): PVC-trigeminy.
Figure 10B:
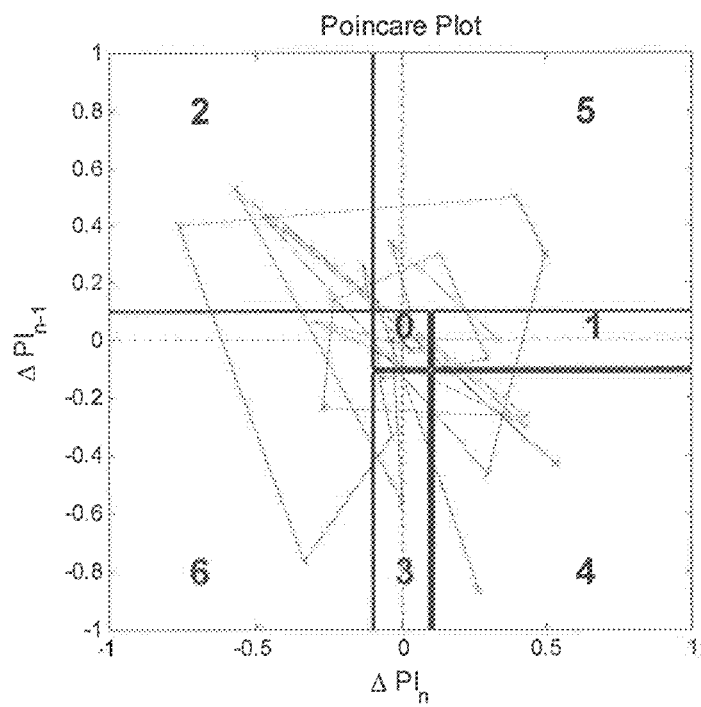
Figure 10C:
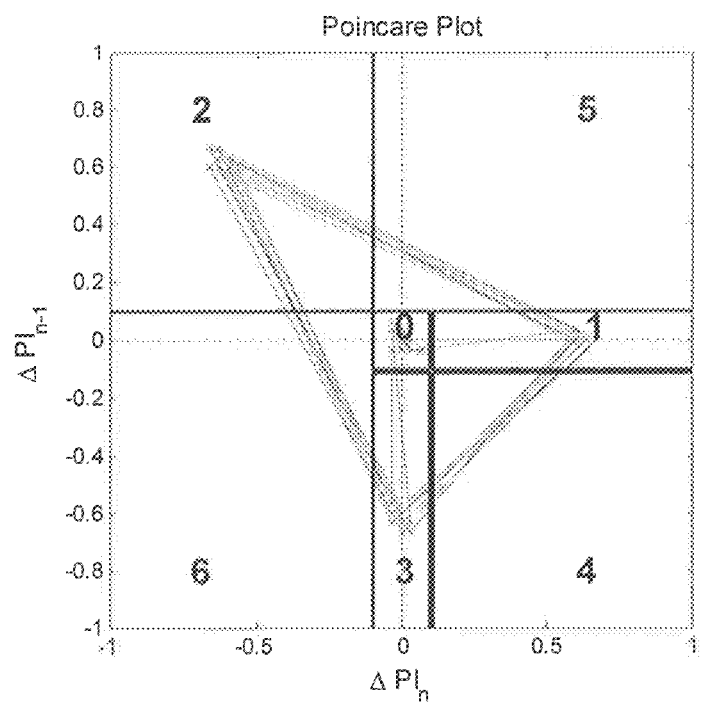
Figure 10D:
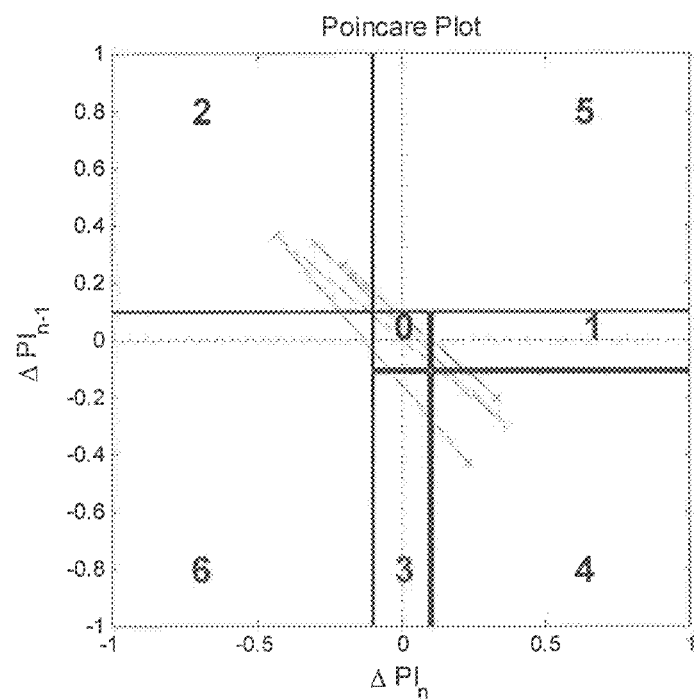

The Poincare pattern for NSR is largely confined within the region "0" as shown in FIG. 10(a) while the Poincare patterns of AF are random and their trajectories cross all six regions as shown in FIG. 10(b). For both PVC and PAC's quadrigeminy, the Poincare plot shows repeating triangle patterns spanning the regions 1, 2 and 3, as shown in FIG. 10(c) as expected in Table II. On the other hand, the trigeminy of the PVC in FIG. 10(d) shows repeating patterns spanning the regions 2 and 4 as described in Table II.

The capability to extract accurate HR signals, heart rate variability dynamics, the respiratory rates and oxygen saturation information directly from the green, red, and blue band signals from a smart phone is detailed in our recently published paper (see also PCX Publication No. WO2012100175, corresponding to PCT/US2012/022049, PHYSIOLOGICAL PARAMETER MONITORING WITH A MOBILE COMMUNICATION DEVICE, filed on Jan. 20, 2012, and corresponding U.S. Published application 2012190947, PHYSIOLOGICAL PARAMETER MONITORING WITH A MOBILE COMMUNICATION DEVICE, which are incorporated by reference herein in their entirety and for ail purposes).

In one or more embodiments, the system of these teachings for physiological parameter monitoring Includes a physiological indicator signal sensing component (sensor) and a mobile communication device having an analysis component analyzing the physiological indicator signal to obtain measurements of one or more physiological, parameters and a motion artifact detection component detecting effects of motion artifacts in the measurements of the one or more physiological parameters.

In one instance, the mobile communication device includes one or more processors and one or more computer usable media, where the computer usable media has computer readable code embodied therein that causes the processor to analyze the physiological indicator signal to obtain measurements of one or more physiological parameters and to detect effects of motion artifacts in the measurements of the one or more physiological parameters. In one or more embodiments, the computer readable code causes the processor to implement the methods described hereinabove.

It should be noted that other embodiments of the mobile communication device, such as the use of ASICs or FPGAs in order to implement the analysis component and/or the motion artifact detection component are within the scope of these teachings.

Figure 11:
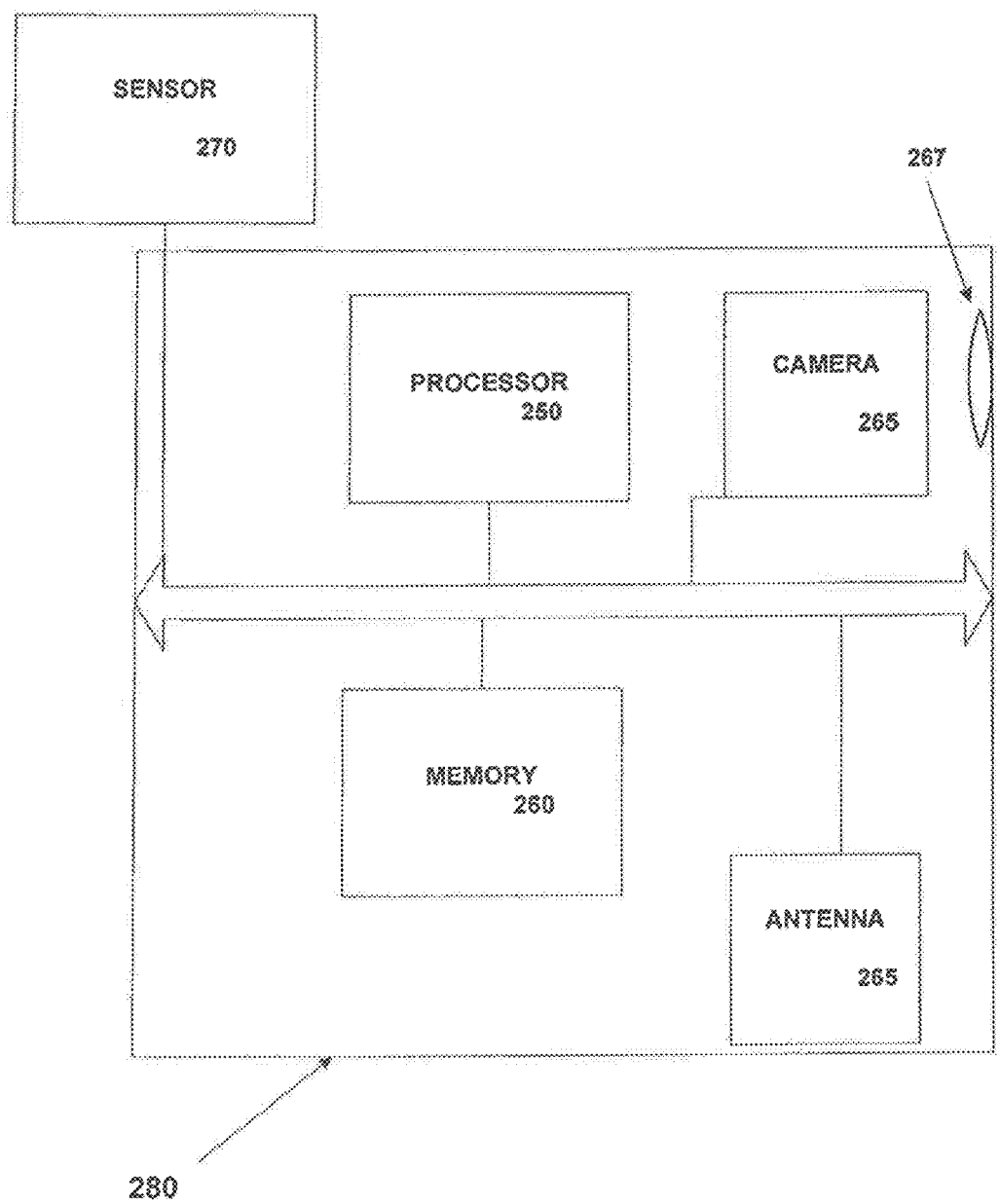
FIG. 11 shows another embodiment of the system of these teachings.

FIG. 11 is a block diagram representation of one embodiment of the system of these teachings. Referring to FIG. 11, in the embodiment shown therein, a mobile communication system 280 includes a processor 250 and one or more memories 260. A physiological indicator signal sensing component (sensor) 270 supplies a physiological indicators signal to the mobile communication device 280. The sensor 270 can be a photoplethysmographic (PPG) sensor or an electrocardiogram (EKG) sensor. In the embodiment shown in FIG. 8, a camera 265, where the camera as an objective lens 267, can also supply the physiological indicators signal to the mobile communication device 280. The one or more memories 260 have computer usable code-embodied therein that causes the processor 250 to that causes the processor to analyze the physiological indicator signal to obtain measurements of one or more physiological parameters and to detect effects of motion artifacts in the measurements of the one or more physiological parameters. In one or more instances, the computer readable code causes the processor 250 to perform the implement the methods described hereinabove.

The one or more memories 260 represent one embodiment of computer usable media having computer readable code embodied therein that causes a processor to implement the methods of these teachings. Embodiments of the method of these teachings are described hereinabove and the computer readable code can cause a processor to implement those embodiments.

In the embodiment shown in FIG. 11, the mobile communication device 280 also includes an antenna 265 that enables communications through one or more of a variety of wireless protocols or over wireless networks. It should be noted that, although the sensor 270 is shown as being directly connected to the mobile communication device 280, embodiments in which the sensor 270 provides the physiological indicators signal to the mobile communication device 280 through a wireless connection are also within the scope of these teachings.

Although these teachings have been described with respect to various embodiments, it should be realized these teachings is also capable of a wide variety of further and other embodiments within the spirit and scope of these teachings.

The invention claimed is:

1. A system for discriminating between normal sinus rhythm without premature ventricular contractions or premature atrial contractions and atrial fibrillation and premature ventricular contractions (PVC) and premature atrial contractions (PACs), the system comprising:
one or more processors; the one or more processors being configured to:
obtain root mean squared of successive differences, Shannon entropy and turning point ratio for peak-to-peak (PPI) interval data;
compare the root mean square of successive differences to a first predetermined threshold;
compare the Shannon entropy to a second predetermined threshold;
compare the turning point ratio to a third predetermined threshold; and
determine, when each of the root mean square of successive differences, the Shannon entropy, and the turning point ratio is less than a corresponding predetermined threshold, a subject under test has normal sinus rhythm without PAC or PVC.

2. A system for discriminating between atrial fibrillation and premature ventricular contractions (PVC) and premature atrial contractions (PACs) and normal sinus rhythm, the system comprising:
one or more processors; the one or more processors being configured to:
obtain root mean squared of successive differences, Shannon entropy and turning point ratio for peak-to-peak (PPI) interval data;
compare the root mean square of successive differences to a first predetermined threshold;
compare the Shannon entropy to a second predetermined threshold;
compare the turning point ratio to a third predetermined threshold;
determine, whether each of the root mean square of successive differences, the Shannon entropy, and the turning point ratio is less than a corresponding predetermined threshold;
wherein not each of the root mean square of successive differences, the Shannon entropy, and the turning point ratio is less than a corresponding predetermined threshold;
demarcate boundaries in a Poincare plot space; the Poincare plot space being a space of time interval between consecutive pulses obtained by sensing variability in heart rate signal;
construct a Poincare plot of time interval data from the PPI data; the time interval being a time interval between consecutive pulses obtained by sensing variability in heart rate signal from the subject under test;
identify repeating patterns in the Poincare plot;
obtain updated data by subtracting the repeating patterns from the time interval data from the subject under test;
obtain root mean squared of successive differences, Shannon entropy and turning point ratio for the updated data;
compare the root mean square of successive differences for the updated data to the first predetermined threshold;
compare the Shannon entropy for the updated data to a second predetermined threshold; compare the turning point ratio for the updated data to the third predetermined threshold; and
determine, when each of the root mean square of successive differences, the Shannon entropy, and the turning point ratio for the updated data is not less than a corresponding predetermined threshold, the subject under test has AF.

3. A system for discriminating between normal sinus rhythm (NSR) with premature ventricular contractions (PVC) or normal sinus rhythm (NSR) with premature atrial contractions (PACs) and normal sinus rhythm without PVC or PAC and atrial fibrillation, the system comprising:
one or more processors; the one or more processors being configured to:
obtain root mean squared of successive differences, Shannon entropy and turning point ratio for peak-to-peak (PPI) interval data;
compare the root mean square of successive differences to a first predetermined threshold;
compare the Shannon entropy to a second predetermined threshold;
compare the turning point ratio to a third predetermined threshold;
determine, whether each of the root mean square of successive differences, the Shannon entropy, and the turning point ratio is less than a corresponding predetermined threshold; wherein not each of the root mean square of successive differences, the Shannon entropy, and the turning point ratio is less than a corresponding predetermined threshold;
demarcate boundaries in a Poincare plot space; the Poincare plot space being a space of time interval between consecutive pulses obtained by sensing variability in heart rate signal;
construct a Poincare plot of time interval data from the PPI data; the time interval being a time interval between consecutive pulses obtained by sensing variability in heart rate signal from the subject under test;
identify repeating patterns in the Poincare plot;
obtain updated data by subtracting the repeating patterns from the time interval data from the subject under test;
obtain root mean squared of successive differences, Shannon entropy and turning point ratio for the updated data;
compare the turning point ratio for the updated data to the third predetermined threshold; wherein each of the root mean square of successive differences, the Shannon entropy, and the turning point ratio for the updated data is less than a corresponding predetermined threshold;

determine pulse rise times and pulse fall-time for a pulse time series from which the PPI data was derived;

determine a difference between pulse rise times of consecutive pulses;

determine a difference between pulse fall times of consecutive pulses;

compare the difference between pulse rise times of consecutive pulses to a fourth predetermined threshold;

compare the difference between pulse fall times of consecutive pulses to a fifth predetermined threshold; and determine from comparison of the difference between pulse rise times of consecutive pulses to the fourth predetermined threshold and comparison of the difference between pulse fall times of consecutive pulses to the fifth predetermined threshold, whether the subject under test has one of normal sinus rhythm (NSR) with PAC or NSR with PVC.

4. The system of claim 3 wherein the one or more processors are further configured to:

determine, when the difference between pulse rise times of consecutive pulses is less than the fourth predetermined threshold and the difference between pulse fall times of consecutive pulses is less than the fifth predetermined threshold, that the subject under test has NSR with PAC.

5. The system of claim 3 wherein the one or more processors are further configured to:

determine, when the difference between pulse rise times of consecutive pulses is not less than the fourth predetermined threshold and the difference between pulse fall times of consecutive pulses is not less than the fifth predetermined threshold, that the subject under test has NSR with PVC.

* * * * *